US007835559B1

(12) United States Patent
Schurman et al.

(10) Patent No.: US 7,835,559 B1
(45) Date of Patent: Nov. 16, 2010

(54) METHOD AND APPARATUS FOR QUANTITATIVE AND COMPARATIVE ANALYSIS OF IMAGE INTENSITIES IN RADIOGRAPHS

(75) Inventors: David J. Schurman, Stanford, CA (US); Robert Lane Smith, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 872 days.

(21) Appl. No.: 11/741,657

(22) Filed: Apr. 27, 2007

(51) Int. Cl.
*G06K 9/00* (2006.01)
*G01N 23/05* (2006.01)
(52) U.S. Cl. .................. 382/128; 250/390.02
(58) Field of Classification Search ............... 382/128, 382/129, 130, 131, 132, 133, 134; 600/407, 600/425, 427, 532; 128/916, 920, 922, 915; 378/4, 8, 21–27, 44, 51, 62, 83, 92, 98.4, 378/101, 140, 901
See application file for complete search history.

(56) References Cited

U.S. PATENT DOCUMENTS 5,384,862 A * 1/1995 Echerer et al. .............. 382/132
5,457,754 A * 10/1995 Han et al. ................... 382/128
5,712,892 A * 1/1998 Weil et al. ..................... 378/54
6,101,408 A * 8/2000 Craine et al. ................ 600/425
6,246,745 B1 * 6/2001 Bi et al. ......................... 378/54
6,687,394 B1 * 2/2004 Mori ........................... 382/132

OTHER PUBLICATIONS

Webpage from The OsteoGram, "Taking 8"×10" Hand X-rays Using CompuMed's Template for OsteoGram Bone Density Analysis," downloaded from www.osteogram.com, 1 page.
C. K. Chow et al., "X-ray Image Substraction by Digital Means," IBM J. Res. Develop. paper, pp. 206-218.
Sher Ee Lim et al., "Detection of Femur and Radius Fractures in X-Ray Images," paper, 8 pages.

\* cited by examiner

*Primary Examiner*—Abolfazl Tabatabai
(74) *Attorney, Agent, or Firm*—Patent Law Group LLP; Carmen C. Cook

(57) ABSTRACT

A system for determining image intensity of a radiograph includes an illuminator for providing lighting to the radiograph, an image reference standard having a predetermined color, a digital imaging device for obtaining a digital image of the radiograph and the image reference standard, a computer for receiving and storing the digital image and for executing programs, and an image analysis program being executed on the computer for providing a first image intensity value of a target area in the radiograph and a second image intensity value of the image reference standard and for computing a normalized image intensity value of the target area using the first and second image intensity values. In one embodiment, the image reference standard is an image reference standard of a black color or a white color.

24 Claims, 4 Drawing Sheets

METHOD AND APPARATUS FOR QUANTITATIVE AND COMPARATIVE ANALYSIS OF IMAGE INTENSITIES IN RADIOGRAPHS

FIELD OF THE INVENTION

The invention relates to a method and an apparatus for analyzing radiographs and, in particular, to a method and an apparatus for analyzing quantitatively image intensities in radiographs.

DESCRIPTION OF THE RELATED ART

Osteoporosis is a bone disorder characterized by the loss of bone mass, and resulting in the increased risk of bone fractures. Bone density measurement is commonly used to detect osteoporosis and is also used as a predictor of the risk of bone fractures in osteoporitic patients. Noninvasive bone density measurement techniques include dual energy x-ray absorptiometry (DEXA) and film based radiographic absorptiometry. In all cases, a patient is exposed to x-rays to acquire an x-ray image of the bones of interest.

Typical DEXA bone densitometer systems require the examination of a body part at more than one x-ray energy level. Thus, at least two x-ray images are required for each examination of a patient. DEXA systems require dedicated equipment and technician to operate. DEXA systems involve time consuming procedures to operate, and require considerable physical space for the equipment. Therefore, DEXA can be prohibitively expensive for some population.

Film-based Radiographic Absorptiometry (RA) is performed by taking a radiograph (also called "an x-ray image") of a body part on a piece of x-ray film. The x-ray film is then digitized and analyzed by a computer. The attenuation in the bone regions of the digital image is used to determine the bone mineral content, while the area of the bone regions is used to compute a projected volume of bone. These two measures can then be used to determine the bone mass. Radiographic absorptiometry technique requires the use of a calibration wedge to be able to accurately calibrate out image variations from a variety of error sources including the x-ray source, positioning of x-ray source to target, film types, and film processing used. Radiographic absorptiometry is typically performed on body extremities, particularly the hand. RA offers the advantage of only requiring a single image per exam, which is captured in a single shot on a piece of x-ray film. Additionally, the x-ray source need not be configured in such a way as to be able to provide x-rays at more than a single energy, as in DEXA devices.

However, using film-based Radiographic Absorptiometry for bone density measurement has certain significant limitations. A significant limitation is that radiographs taken at different times or taken using different x-ray machines or under different x-ray conditions cannot be use for quantitative bone densities comparisons. This is because radiographs have inherent variations, such as the x-ray source, the distance between the x-ray source and the object, the x-ray power used, and also the processing used to develop the x-ray film. For instance, x-ray images of a patient taken over a period of time cannot be of use to provide quantitative bone density data of that patient and to determine if there has been bone loss over time.

Even when the radiographs are taken using a calibration wedge, the calibration wedge cannot be used to remove the aforementioned errors in the radiographs unless the same calibration wedge is used for all the radiographs, all the radiographs are taken under the same x-ray conditions and all the radiographs are developed under the same processing conditions. Otherwise, the image of the calibration wedge in the x-ray film merely reproduces all the variations under which the x-ray image is obtain. For instance, U.S. Pat. No. 6,246,745 to Bi et al. describes a bone density measurement system where an x-ray file is scanned by a scanner and then bone density measurements are made from the digitized x-ray image. However, Bi requires the use of a calibration wedge in each x-ray image. The calibration wedge has to be the same for each x-ray image and x-ray image has to be taken under the same conditions. Only when these specific conditions are met can the radiographs be used for quantitative comparison.

SUMMARY OF THE INVENTION

According to one embodiment of the present invention, a system for determining image intensity of a radiograph includes an illuminator for providing lighting to the radiograph, an image reference standard having a predetermined color, a digital imaging device for obtaining a digital image of the radiograph and the image reference standard, a computer for receiving and storing the digital image and for executing programs, and an image analysis program being executed on the computer for providing a first image intensity value of a target area in the radiograph and a second image intensity value of the image reference standard and for computing a normalized image intensity value of the target area using the first and second image intensity values.

In one embodiment, the image reference standard is an image reference standard of a black color or a white color.

According to another aspect of the present invention, a method for determining image intensity of a radiograph includes providing illumination to the radiograph, providing an image reference standard of a predetermined color, obtaining a digital image of the radiograph and the image reference standard, exporting the digital image to a computer, determining a first image intensity value of a target area using an image analysis program executed on the computer, determining a second image intensity value of the image reference standard using the image analysis program executed on the computer, and normalizing the first image intensity value using the second image intensity value to provide a normalized image intensity value being indicative of the image intensity of the target area The present invention is better understood upon consideration of the detailed description below and the accompanying drawings.

DETAILED DESCRIPTION OF THE PREFERRED EMBODIMENTS

Figure 1:
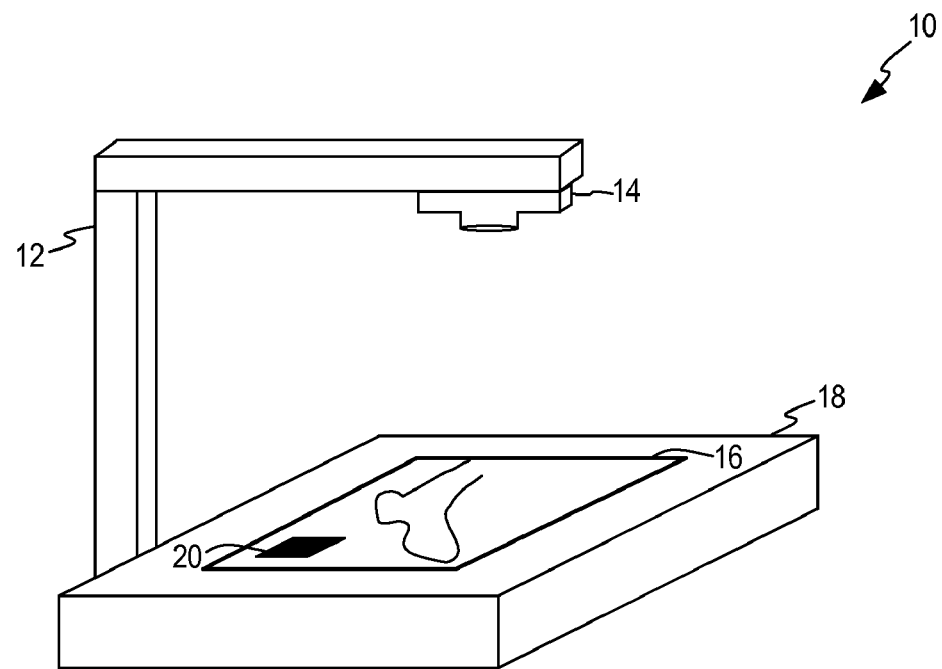
FIG. 1 illustrates a radiograph image intensity measurement system according to one embodiment of the present invention.
Figure 1:
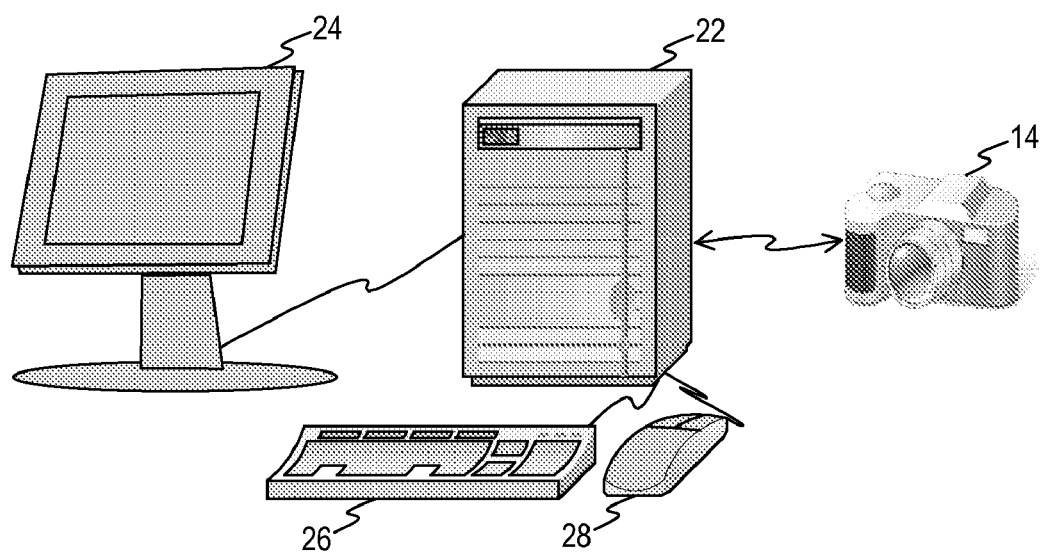

In accordance with the principles of the present invention, a radiograph image intensity measurement system includes a digital imaging device, an image reference standard, an illuminator, a computer, and an image analysis program. The radiograph image intensity measurement system obtains a digital image of a target area in the radiograph and the image reference standard. The image analysis program measures the image intensity values of the target area and the image reference standard and computes a normalized image intensity value of the target area. By referencing the image intensity value of a target area to the image intensity value of the image reference standard, the normalized image intensity value obtained for one radiograph can be compared quantitatively to the normalized image intensity value of another radiograph, even when the radiographs are taken under different x-ray conditions.

More specifically, the image analysis program implements a normalization algorithm for computing normalized image intensity values from one or more radiographs. The normalized image intensity values are indicative of quantitative results of the gray scale variations of the radiographs. In other embodiments, the radiograph image intensity measurement system and method of the present invention can also be applied to compare color variations in digital images, as will be described in more detail below.

The radiograph image intensity measurement system and associated method of the present invention provides many advantages over conventional systems and methods. First, the radiograph image intensity measurement system and method of the present invention allow radiographs taken under different conditions to be compared quantitatively. Such quantitative comparison was not possible in the past unless the radiographs are taken under the same x-ray conditions and more specifically, the radiographs have to be taken with the same calibration wedge. Variations in x-ray conditions, such as the x-ray source, positioning between the source and the object, the film type, and film processing used, all contribute to errors in the x-ray intensity values of the x-ray image. Therefore, prior to the present invention, it was not possible to compare quantitatively the image intensity values of one x-ray film to another.

The radiograph image intensity measurement system and method of the present invention provides a cost effective way to measure and quantify bone densities, such as for monitoring osteoporosis in a patient. X-ray images of a patient taken over time can be analyzed to determine changes in the patient's bone density over time by comparing the normalized image intensity values of x-ray images of the patient. The system and method of the present invention circumvents the inherent variations in x-ray images taken under different, uncontrolled conditions by using the image reference standard during digital imaging. Therefore, the system and method of the present invention allow recurrent analysis of bone density of a specific location of a patient over time to monitor the comparative changes of the patient's bone density at that location.

Furthermore, the radiograph image intensity measurement system and method of the present invention can also be used to compare quantitatively x-ray images of different bone locations of a patient. For example, an x-ray image of the femoral head can be compared to an x-ray image of the tibia to determine differences in bone density for that patient at the different bone locations.

Lastly, the radiograph image intensity measurement system and method of the present invention enables bone density changes in a person to be determined without subjecting patients to an excessive amount of x-ray radiation. It has been reported that any increase in x-ray radiation exposure is hazardous. Bone density measurement methods such as DEXA are sometimes undesirable as patients are subjected to an increased amount of radiation.

FIG. 1 illustrates a radiograph image intensity measurement system according to one embodiment of the present invention. Referring to FIG. 1, a radiograph image intensity measurement system 10 (system 10) includes an illuminator 18, an image reference standard 20, a digital imaging device 14, a personal computer 22, and an image analysis program being stored on and executed by personal computer 22. The radiograph image intensity measurement system 10 is provided for analyzing radiographs, such as a radiograph 16 of a femur bone. The image reference standard 20 is placed on or near radiograph 16 to be photographed by digital imaging device 14 to obtain a digital image of the radiograph 16 together with the image reference standard 20.

Radiograph image intensity measurement system 10 is configured to analyze x-ray films which are photographic negative films. Radiograph image intensity measurement system 10 can also be used to analyze digital x-ray images such as those stored on a computer. In that case, the computerized digital x-ray images are visualized onto a film negative for use with system 10.

In the present embodiment, a radiograph illuminator 18, such as a light box, is used to provide backside illumination to radiograph 16 which is an x-ray negative film. In other embodiments, other types of light box or illumination device can be used to provide back-side illumination to the x-ray negative film. Furthermore, in other embodiments, the illuminator 18 can provide visible light, or ultraviolet (UV) light or infrared light depending on the nature of the radiograph to be analyzed. For example, UV light is used when the radiograph to be analyzed contains DNA data.

In the present embodiment, digital imaging device 14 is mounted on an adjustable support arm 12 to anchor and position the digital imaging device to facilitate the imaging of radiographs 16 and image reference standard 20. Mounting of digital imaging device 14 to the adjustable support arm 12 allows the field of view and focus of the digital imaging device to be readily adjusted. Support arm 12 in FIG. 1 is illustrative only and is not intended to be limiting. Moreover, support arm 12 is optional and may be omitted in other embodiments. The digital image device 14 may be held by the user to obtain the digital image of the radiograph and the image reference standard. In yet other embodiments, other support structure can be used to anchor and position digital imaging device 14 to facilitate imaging.

Image reference standard 20 is a user defined standard of any color, including black and white. For gray scale images with a black background, such as an x-ray negative film, a black color reference is often used. The image reference standard 20 can also include multiple color references for use in comparative color analysis. In the present embodiment, image reference standard 20 is assumed to be a black color card. Image reference standard 20 is to be placed on or near the radiograph to be photographed with the radiograph. Image reference standard 20 should be placed outside of the target area of interest of the radiograph but within the field of view of digital imaging device 14.

Figure 2:
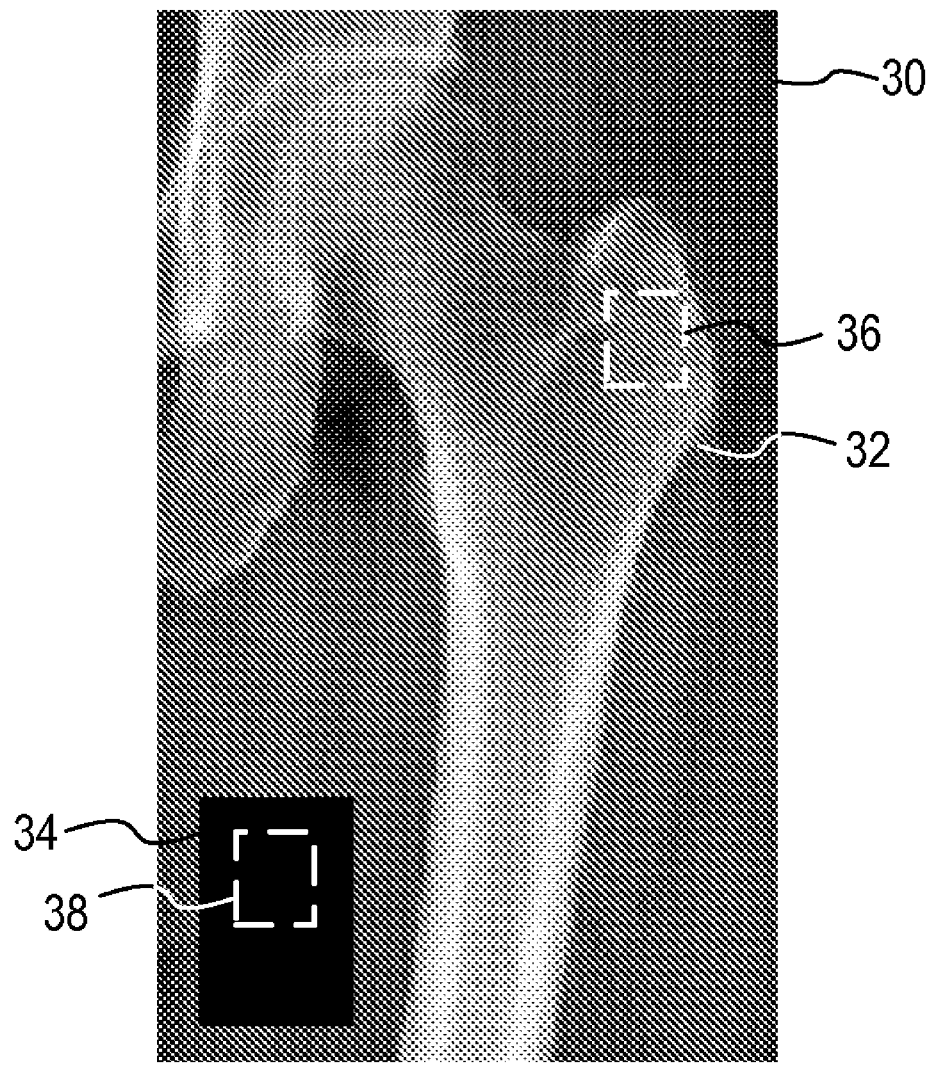
FIG. 2 illustrates a digitized image of a radiograph of a femur bone and an image reference standard.

Digital imaging device 14 can be any digital cameras currently available or to be developed. For example, digital imaging device 14 can be a CMOS digital camera or a CCD digital camera. After capturing the digital image of the radiograph and the image reference standard, digital imaging device 14 is coupled to personal computer 22 where the digital image or images are exported onto personal computer 22 for analysis. FIG. 2 illustrates a representative digitized image of a radiograph of a femur bone and an image reference standard. Digitized image 30 of FIG. 2 includes an x-ray image of a femur bone 32 and the image reference standard 34.

Personal computer 22 may include a monitor 24, a keyboard 26 and a mouse 28 to enable a user to control and operate the personal computer. Personal computer 22 includes sufficient memory for storing one or more digital images and a processor for executing the image analysis program. In one embodiment, the image analysis program is the "NIH Image" program. NIH Image is a public domain image processing and analysis program for the Macintosh developed at the Research Services Branch (RSB) of the National Institute of Mental Health (NIMH), part of the National Institutes of Health (NIH). NIH Image is available for download from the website http://rsb.info.nih.gov/nih-image/. In another embodiment, the image analysis program is the "ImageJ" image processing and analysis program which is a Java version of NIH Image that can be run on any operating systems, PC or Macintosh. ImageJ is available from the same website as NIH Image. In yet another embodiment, the image analysis program is the commercially available program Adobe Photoshop, available from Adobe Systems Incorporated, San Jose, Calif. (www.adobe.com).

Furthermore, in one embodiment, computer 22 also executes instructions to apply a normalization formula to image intensity values obtained from the digital image of the radiograph and the image reference standard. The normalization formula provides comparative analysis of radiographs taken under different x-ray conditions, as will be described in more detail below.

Figure 3:
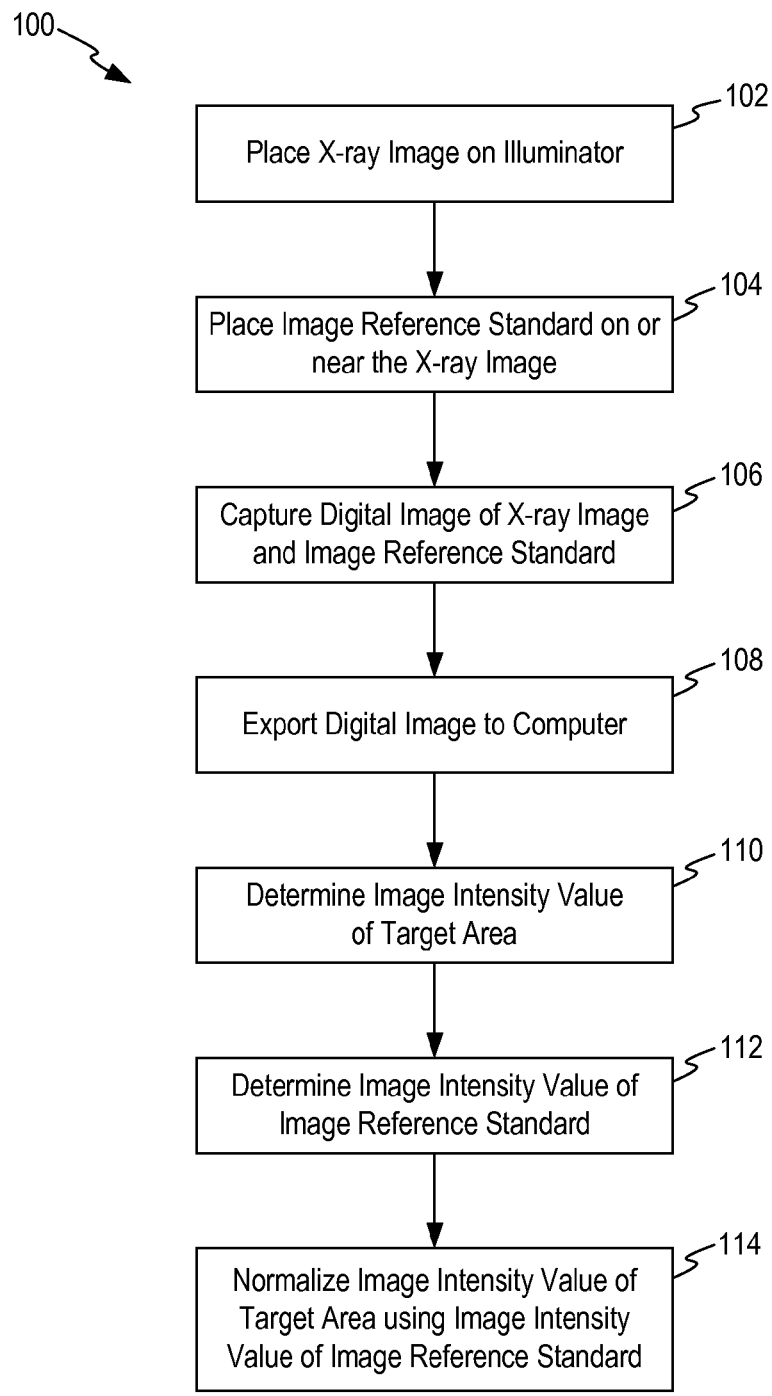
FIG. 3 is a flow chart illustrating the operation of the radiograph image intensity measurement system according to one embodiment of the present invention.

The operation of the radiograph image intensity measurement system will now be described with reference to the flow chart in FIG. 3. FIG. 3 is a flow chart illustrating the operation of the radiograph image intensity measurement system according to one embodiment of the present invention. Referring to FIG. 3, radiograph image intensity measurement method 100 ("method 100") starts by placing the radiograph or x-ray image to be analyzed on an illuminator, such as a light box (step 102). Then, the image reference standard is placed on or near the radiograph (step 104). The target area of the radiograph and the image reference standard should both be within the field of view of the digital imaging device.

Method 100 continues with capturing a digital image of the radiograph and the image reference standard using the digital imaging device (step 106). The digital image is captured with lighting provided by the illuminator. The captured digital image of the radiograph and the image reference standard is then exported to a computer to be processed (step 108). In the present description, it is assumed that the radiograph being analyzed is the x-ray image of FIG. 2 and the radiograph is examined for bone density measurement. The computer thus receives a digital image 30 including a digitized image of the x-ray image of the femur bone 36 and a digitized image of the image reference standard 34.

The digital image is then analyzed using an image analysis program such as NIH Image, ImageJ or Adobe Photoshop. In the present embodiment, the image intensity value of the target area is obtained using the image analysis program (step 110). The image intensity value of the image reference standard is also obtained (step 112). Note that the order of obtaining the image intensity values is not critical to the practice of the present invention. That is, the image intensity value of the image reference standard can be obtained first before the image intensity value of the target area. Then, the image intensity value of the image reference standard is used to normalize the image intensity of the target area (step 114).

For instance, referring to FIG. 2, the target area of interest in the radiograph is the femur bone 32. The image analysis program provides a drawing tool to allow a user to select an analysis area 36 in the target bone. The size and dimension of the analysis area is user defined. Once the analysis area, such as area 36, is defined, the image analysis is used to provide a histogram of the image intensity values in analysis area 36. From the histogram, the average or mean image intensity value is also obtained and used as the image intensity value indicative of the analysis area 36.

The drawing tool is also used to select an analysis area 38 in the image reference standard. A histogram of the image intensity values in analysis area 38 is also obtained and the average or mean image intensity value is used as the image intensity value indicative of analysis area 38. When the image intensity value of the target bone area and the image intensity of the image reference standard are computed, a normalized image intensity value for the target bone area is then computed, such as by dividing the image intensity value of the target bone area by the image intensity value of the image reference standard. That is:

$$II_{normalized} = \frac{II_{target\_area}}{II_{image\_ref}}.$$

The normalized image intensity value of the target bone area is indicative of the bone density of the target bone.

Method 100 can be applied to compare image intensity values at multiple locations on the same radiograph. In that case, an analysis area is drawn over each area of interested and the image intensity value of each analysis area is referenced to the image intensity value of the image reference standard to be normalized.

Figure 4:
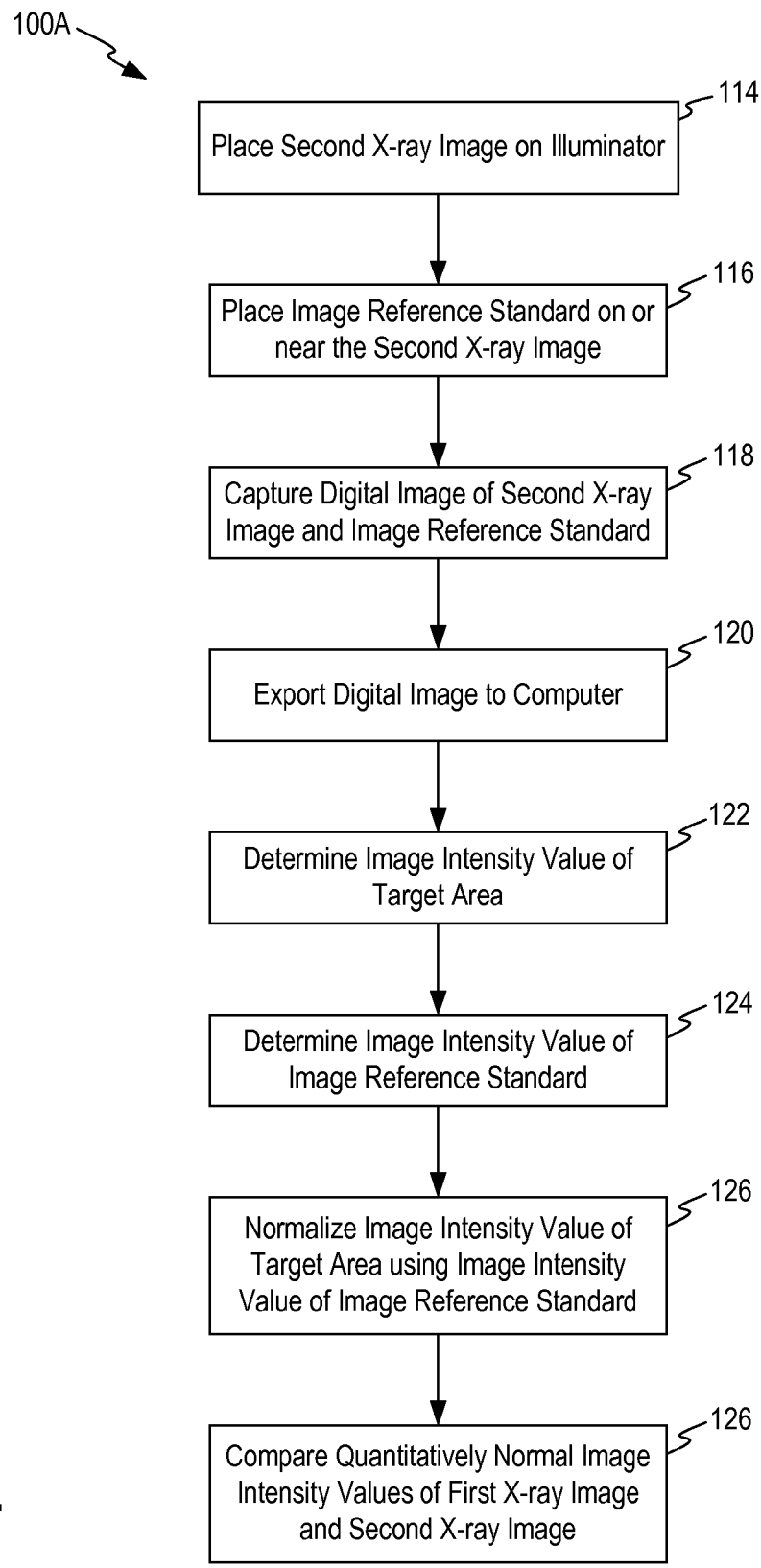
FIG. 4 is a flow chart illustrating the operation of the radiograph image intensity measurement system according to a second embodiment of the present invention.

In other applications, it is desirable to analyze multiple radiographs, such as radiographs of a patient taken over time, and to provide quantitative comparisons of the radiographs. According to another embodiment of the present invention, radiograph image intensity measurement method 100 can be repeated to analyze one or more radiographs and to provide normalized image intensity values that can be quantitatively compared. FIG. 4 is a flow chart illustrating the operation of the radiograph image intensity measurement system according to a second embodiment of the present invention. FIG. 4 in fact is a continuation and a repetition of method 100 of FIG. 3.

Referring to FIG. 4, after a first radiograph is analysis using method 100 of FIG. 3, method 100A continues by analyzing a second radiograph. The second radiograph is placed on the illumination (step 114). The image reference standard is placed on or near the second radiograph (step 116). The digital imaging device captures the image of the second radiograph and the image reference standard (step 118). The digital image is exported to the computer (step 120). Then, in the same manner as performed for the first radiograph, the image intensity value of the target area and the image intensity value of the image reference standard are obtained (steps 122, 124). A normalized image intensity value of the target area is computed (step 126).

The normalized image intensity value from the first radiograph can be compared quantitatively to the normalized image intensity value of the second radiograph (step 128). For example, the two normalized image intensity values can be compared to determine changes in bone density from one x-ray to another. Changes in bone density can be computed as a difference between the normalized image intensity value of a first radiograph and the normalized image intensity value of a second radiograph. Many other applications of method 100/100A are possible because method 100/100A enables the quantitative comparison of the normalized image intensity values of multiple x-ray images taken under different, uncontrolled conditions.

In one embodiment, the imaging analysis program uses an 8-bit gray scale range. In digital imaging, an image intensity value of 0 denotes the black color and the image intensity value of 255 denotes the white color. However, due to different x-ray conditions and film processing conditions, each radiograph exhibits different image intensity range. By using an image reference standard in accordance of the present invention, the image intensity range is re-referenced to the ideal case where black is 0 and white is 255 so that meaningful quantitative comparisons between radiographs can be made. The image reference standard provides the basis for comparing multiple x-ray images regardless of the variety of variance under which the x-ray images are taken. The x-ray images may be taken at different distance, voltage, alignment and angle but these variances are rectified by the image reference standard.

According to another embodiment of the present invention, the digital image of the radiograph can be artificially colored so that the gray scale range is represented by a range of colors. In that case, the image reference standard can be a color reference and does not have to be black or white.

According to another aspect of the present invention, the system and method of the present invention can also be used for color calibration. In that case, the desired color is used as the image reference standard. A digital image of a color printout and the image reference standard is taken. The image intensity value of the desired color can be computed together with the image intensity value of the image reference standard. The normalized image intensity value of the desired color can be used as an indicator of any change in the desired color tone.

The above detailed descriptions are provided to illustrate specific embodiments of the present invention and are not intended to be limiting. Numerous modifications and variations within the scope of the present invention are possible. The present invention is defined by the appended claims.

We claim:

1. A system for determining image intensity of a radiograph, comprising:
   an illuminator for providing lighting to the radiograph;
   an image reference standard having a predetermined color;
   a digital imaging device for obtaining a digital image of the radiograph and the image reference standard;
   a computer for receiving and storing the digital image and for executing programs; and
   an image analysis program being executed on the computer for providing from the digital image a first image intensity value of a target area in the radiograph and a second image intensity value of the image reference standard and for computing a normalized image intensity value of the target area using the first and second image intensity values.

2. The system of claim 1, wherein the image reference standard comprises an image reference standard of a black color or a white color.

3. The system of claim 1, wherein the illuminator comprises a light box providing backlight to the radiograph, the radiograph being placed on the light box and the image reference standard being placed on or near the radiograph within a field of view of the digital imaging device but away from the target area.

4. The system of claim 3, wherein the illuminator comprises a light box providing one of a visible light, an ultraviolet light, and an infrared light as backlight to the radiograph.

5. The system of claim 1, wherein the digital imaging device comprises a digital camera.

6. The system of claim 5, further comprising an adjustable support arm to which the digital imaging device is mounted.

7. The system of claim 1, wherein the image analysis program provides the first image intensity value of the target area by obtaining a histogram of image intensity values for a first analysis area within the target area, and computing a mean or an average image intensity value from the histogram, the mean image intensity value being the first image intensity value.

8. The system of claim 1, wherein the image analysis program provides the second image intensity value of the image reference standard by obtaining a histogram of image intensity values for the image reference standard, and computing a mean or an average image intensity value from the histogram, the mean image intensity value being the second image intensity value.

9. The system of claim 1, wherein the radiograph comprises a first radiograph of a target bone and the system further determines the image intensity of a second radiograph of the target bone, the first radiograph and the second radiograph being obtained under different x-ray conditions or at different times, the image analysis program being executed on the computer for receiving a digital image of the second radiograph, for providing a third image intensity value from the digital image of the target area on the second radiograph and a fourth image intensity value from the digital image of the image reference standard on the second radiograph and for computing a normalized image intensity value of the target area using the third and fourth image intensity values.

10. The system of claim 9, wherein the image analysis program being executed on the computer compares quantitatively the normalized image intensity value obtained from the first radiograph and the normalized image intensity value obtained from the second radiograph to determine a change in bone density between the first radiograph and the second radiograph.

11. The system of claim 10, wherein the image analysis program being executed on the computer computes a first normalized image intensity value by dividing the first image intensity value by the second image intensity value and computes a second normalized image intensity value by dividing the third image intensity value by the fourth image intensity value, the image analysis program being executed to subtract the second normalized image intensity value from the first normalized image intensity value to provide a quantitative comparison of the bone densities in the first radiograph and the second radiograph.

12. The system of claim 10, wherein the image analysis program comprises one of NIH Image, ImageJ and Photoshop.

13. The system of claim 10, wherein the image analysis program analyzes the digital image in gray scale.

14. The system of claim 10, wherein the image analysis program analyzes the digital image in color, the digital image being artificially colored.

15. A method for determining image intensity of a radiograph, comprising:
   providing illumination to the radiograph;
   providing an image reference standard of a predetermined color;

obtaining a digital image of the radiograph and the image reference standard;

exporting the digital image to a computer;

determining from the digital image a first image intensity value of a target area using an image analysis program executed on the computer;

determining from the digital image a second image intensity value of the image reference standard using the image analysis program executed on the computer; and normalizing the first image intensity value using the second image intensity value to provide a normalized image intensity value being indicative of the image intensity of the target area.

16. The method of claim 15, wherein providing an image reference standard comprises providing an image reference standard of a black color or a white color.

17. The method of claim 15, wherein obtaining a digital image of the radiograph and the image reference standard comprises:

placing the radiograph on a light box;

placing the image reference standard on or near the radiograph within a field of view of a digital imaging device but away from the target area; and obtaining a digital image using the digital imaging device.

18. The method of claim 17, wherein obtaining a digital image using the digital imaging device comprises obtaining a digital image using a digital camera.

19. The method of claim 17, wherein placing the radiograph on a light box comprises placing the radiograph on a light box providing one of a visible light, an ultra-violet light and an infrared light.

20. The method of claim 15, wherein determining from the digital image a first image intensity value of a target area using an image analysis program executed on the computer comprises:

obtaining a histogram of image intensity values of a first analysis area within the target area using the image analysis program; and computing a mean or an average image intensity value from the histogram, the mean image intensity value being the first image intensity value.

21. The method of claim 15, wherein determining from the digital image a second image intensity value of the image reference standard using the image analysis program executed on the computer comprises:

obtaining a histogram of image intensity values for the image reference standard using the image analysis program; and computing a mean or an average image intensity value from the histogram, the mean image intensity value being the second image intensity value.

22. The method of claim 15, wherein the radiograph comprises a first radiograph of a target bone and the method determines the image intensity of a second radiograph of the target bone, the first radiograph and the second radiograph being obtained under different x-ray conditions or at different times, the method further comprising:

providing illumination to the second radiograph, providing the image reference standard on or near the second radiograph;

obtaining a digital image of the second radiograph and the image reference standard;

exporting the digital image to the computer;

determining from the digital image a third image intensity value of a target area using the image analysis program executed on the computer;

determining from the digital image a fourth image intensity value of the image reference standard using the image analysis program executed on the computer;

normalizing the third image intensity value using the fourth image intensity value to provide a normalized image intensity value being indicative of the image intensity of the target area in the second radiograph; and comparing quantitatively the normalized image intensity value obtained from the first radiograph and the normalized image intensity value obtained from the second radiograph to determine a change in bone density between the first radiograph and the second radiograph.

23. The method of claim 22, wherein:

normalizing the first image intensity value using the second image intensity value comprises dividing the first image intensity value by the second image intensity value to obtain a first normalized image intensity value;

normalizing the third image intensity value using the fourth image intensity comprises dividing the third image intensity value by the fourth image intensity value to obtain a second normalized image intensity value; and comparing quantitatively the normalized image intensity value obtained from the first radiograph and the normalized image intensity value obtained from the second radiograph comprises subtracting the second normalized image intensity value from the first normalized image intensity value.

24. The method of claim 15, further comprising:

artificially coloring the digital image.

* * * * *